(12) United States Patent
Kakinuma

(10) Patent No.: US 10,384,999 B2
(45) Date of Patent: Aug. 20, 2019

(54) METHOD OF PRODUCING 2-HYDROXY-1,4-NAPHTHOQUINONE

(71) Applicant: AGRO-KANESHO CO., LTD., Minato-ku (JP)

(72) Inventor: Seiji Kakinuma, Misato (JP)

(73) Assignee: AGRO-KANESHO CO., LTD., Minato-ku (JP)

( * ) Notice: Subject to any disclaimer, the term of this patent is extended or adjusted under 35 U.S.C. 154(b) by 0 days.

(21) Appl. No.: 15/747,256

(22) PCT Filed: Jun. 24, 2016

(86) PCT No.: PCT/JP2016/068869
§ 371 (c)(1),
(2) Date: Jan. 24, 2018

(87) PCT Pub. No.: WO2017/033557
PCT Pub. Date: Mar. 2, 2017

(65) Prior Publication Data
US 2018/0215693 A1   Aug. 2, 2018

(30) Foreign Application Priority Data

Aug. 21, 2015 (JP) ................. 2015-163536

(51) Int. Cl.
*C07C 46/00* (2006.01)
*B01J 23/00* (2006.01)
*C07C 46/04* (2006.01)
*B01J 23/22* (2006.01)
*C07B 61/00* (2006.01)

(52) U.S. Cl.
CPC ............. *C07C 46/04* (2013.01); *B01J 23/22* (2013.01); *C07B 61/00* (2013.01); *C07C 2602/10* (2017.05)

(58) Field of Classification Search
CPC .................. C07C 46/04; B01J 23/22
See application file for complete search history.

(56) References Cited

PUBLICATIONS

Zhao, et al., "Cobalt Porphyrins Immobilized on Polymer Microspheres as Catalysts for the Oxidation of 2-naphthol to 2-hydroxy-1,4-naphthoquinone by Molecular Oxygen", Catalysis Letters, vol. 141, No. 12, Published online: Oct. 18, 2011, pp. 1808-1813.
Nagase, et al., "Oxidation of Naphthols with Hydrogen Peroxide in Alkaline Media", Journal of the Pharmaceutical Society of Japan, vol. 74, No. 1, 1954, pp. 9-13 (with English Abstract).
International Search Report dated Sep. 6, 2016 in PCT/JP2016/068869 filed Jun. 24, 2016.

*Primary Examiner* — Sikarl A Witherspoon
(74) *Attorney, Agent, or Firm* — Oblon, McClelland, Maier & Neustadt, L.L.P.

(57) ABSTRACT

Provided is a method of producing 2-hydroxy-1,4-naphthoquinone in a large amount, a high yield, and inexpensively. This method comprises oxidizing 2-hydroxynaphthalene with hydrogen peroxide in (1) an alkaline aqueous solution or in (2) a mixture of an alkaline aqueous solution with an inert organic solvent incompatible with water, in the presence of a vanadium catalyst.

4 Claims, No Drawings

METHOD OF PRODUCING 2-HYDROXY-1,4-NAPHTHOQUINONE

BACKGROUND OF THE INVENTION

Field of the Invention

The present invention relates to a method of producing 2-hydroxy-1,4-naphthoquinone. Specifically, the invention relates to a method of producing 2-hydroxy-1,4-naphthoquinone, which is useful as, for example, a raw material for producing a resin, an intermediate of a face wash, or an intermediate of a pharmaceutical or agricultural chemical, in a high yield and a high purity.

Background Technology

As a method of producing 2-hydroxy-1,4-naphthoquinone using 2-hydroxynaphthalene (or 2-naphthol) as a raw material, there is disclosed a method of oxidizing 2-hydroxynaphthalene with gaseous oxygen in methanol in the presence of a cobalt catalyst and a caustic alkali. However, in this method, an expensive catalyst, such as a cobalt morpholine catalyst fixed to a polymer, must be used. In addition, the yield is insufficient. This method is described in the following non-patent document 1.

As a method of producing 2-hydroxy-1,4-naphthoquinone using 1-hydroxynaphthalene as a raw material, there is disclosed a method of oxidizing 1-hydroxynaphthalene with hydrogen peroxide in an aqueous potassium hydroxide solution in the presence of a vanadium catalyst. However, in this method, 1-naphthol used as a raw material is expensive, and also the yield is low. Thus, there is a problem of cost. This method is described in the following non-patent document 2.

PRIOR ART REFERENCES

Non-patent document 1: Catalysis Letters, Vol. 141, No. 12, p. 1808 (2011)

Non-patent document 2: Yakugaku Zasshi Vol. 74, No. 1, p. 9 (1954)

DESCRIPTION OF THE INVENTION

Subject to be Resolved

The present inventors have diligently studied about a method that can produce 2-hydroxy-1,4-naphthoquinone industrially easily, in a large amount, and in a high yield at a low cost and have arrived at the present invention.

Means for Resolving the Subject

The present inventor has intensively made studies for solving the above-mentioned problems and, as a result, have found that 2-hydroxy-1,4-naphthoquinone can be obtained in a high yield and a high purity by oxidizing 2-hydroxynaphthalene with hydrogen peroxide in (1) an alkaline solution or in (2) a mixture of an alkaline solution with an inert organic solvent incompatible with water, in the presence of a vanadium catalyst. The present invention has been thus accomplished.

The present invention relates to a method of producing 2-hydroxy-1,4-naphthoquinone represented by Formula [I]:

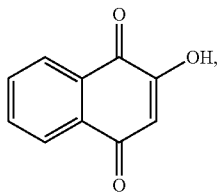 [SMILES: O=C1C=C(O)C(=O)c2ccccc21]

comprising oxidizing 2-hydroxynaphthalene represented by Formula [II]:

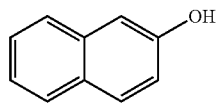

with hydrogen peroxide in (1) an alkaline aqueous solution or in (2) a mixture of an alkaline aqueous solution with an inert organic solvent incompatible with water, in the presence of a vanadium catalyst.

EMBODIMENTS FOR CARRYING OUT THE INVENTION

The present invention will now be described in detail below.

2-hydroxynaphthalene represented by Formula [II] used as a starting material in the present invention is a known compound and readily commercially available.

In the present invention, for example, a 5% to 50% alkaline aqueous solution, preferably, a 20% to 30% alkaline aqueous solution is added to 2-hydroxynaphthalene such that the molar amount of the alkali is, for example, 1 to 100 times, preferably, 2 to 10 times in relation to 2-hydroxynaphthalene; and a vanadium catalyst, such as vanadium (V) oxide, is added to the alkaline aqueous solution such that the amount of the catalyst is, for example, 0.01 to 50 mass %, preferably, 0.1 to 5 mass % in relation to 2-hydroxynaphthalene. To the resultant solution, for example, 10% to 60% hydrogen peroxide, preferably, 30% to 40% hydrogen peroxide is added such that the molar amount of hydrogen peroxide is, for example, 1 to 20 times, preferably, 3 to 10 times in relation to 2-hydroxynaphthalene, for example, at 30° C. to 90° C., for example, over 1 to 20 hours, preferably at 40° C. to 60° C., for example, over 3 to 10 hours. After the reaction, in order to obtain the compound represented by Formula [I], an acid, such as hydrochloric acid, is added to the reaction solution in an amount, for example, such that the molar amount of the acid is, for example, 1 to 5 times, preferably, 1.1 to 2 times in relation to the alkali to make the solution acidic and the precipitated crystals are collected by filtration. The collected crystals are washed with water and are then dried. Thus, the compound represented by Formula [I] as the target compound can be significantly easily obtained in a high yield and a high purity. This reaction can be performed under coexistence of an inert organic solvent incompatible with water.

The vanadium catalyst used in the present invention may have any composition so long as it contains a vanadium oxide as a component and catalyzes the conversion of 2-hydroxynaphthalene into 2-hydroxy-1,4-naphthoquinone. Specifically, for example, vanadium (III) oxide, vanadium (IV) oxide, vanadium (V) oxide, ammonium metavanadate, or potassium vanadate can be used. In particular, vanadium (V) oxide is preferred.

The reaction is performed in an alkaline solution or in a mixture of an alkaline solution and an inert organic solvent incompatible with water. The alkali is preferably an alkali metal and is particularly preferably a hydroxide of an alkali metal. Specifically, the alkali is preferably sodium hydroxide or potassium hydroxide. These alkalis may be used alone or can be used as a mixture thereof.

When the oxidation reaction of the present invention is performed in a mixture of an alkaline solution with an organic solvent, the organic solvent may be any solvent so long as it does not substantially affect the progress of the reaction. Specifically, preferred are various kinds of aromatic hydrocarbons, such as benzene, toluene, xylene, and chlorobenzene; and various kinds of cyclic or acyclic aliphatic hydrocarbons, such as pentane, hexane, heptane, and cyclohexane. Particularly, the inert organic solvent is preferably toluene.

It is suitable that the amount of the organic solvent to be used is, for example, 0.01 to 10 times, preferably, 0.1 to 2 times as much as the alkaline solution.

In the present invention, the oxidation reaction is generally performed at 10° C. to 100° C., preferably, at 30° C. to 60° C.

The concentration of the acid, such as hydrochloric acid, is 1% to 100%, preferably, 20% to 100%.

The reaction solution is preferably cooled to, for example, 60° C. to 0° C., preferably, 30° C. to 5° C.

The production method of the present invention is a method of preparing 2-hydroxy-1,4-naphthoquinone in a high yield and a high purity, by oxidizing 2-hydroxynaphthalene with a hydrogen peroxide solution in (1) an alkaline solution or in (2) a mixture of an alkaline aqueous solution with an inert organic solvent incompatible with water, in the presence of a vanadium catalyst.

EXAMPLE

The present invention will now be further described in detail by way of examples, but the scope of the invention is not limited to the examples.

Example 1

Synthesis of 2-hydroxy-1,4-naphthoquinone

Vanadium (V) oxide (273 mg), toluene (30 mL), and 2-hydroxynaphthalene (7.20 g) were added to a 28% aqueous sodium hydroxide solution (35.8 g), and then a 35% hydrogen peroxide solution (29.1 g) was dropwise added thereto at 45° C. over 4 hours. To the reaction solution, 35% hydrochloric acid (31.3 g) was dropwise added. The reaction solution was cooled to 10° C. The resultant precipitated crystals were collected by filtration and were further washed with water and were air dried to obtain 2-hydroxy-1,4-naphthoquinone (6.6 g, yield: 90%). The purity was 99%. Herein, the molar ratio of the alkali to 2-hydroxynaphthalene was 5 times; the amount of the vanadium catalyst was 3.8 mass % based on the amount of 2-hydroxynaphthalene; and the molar ratio of hydrogen peroxide to 2-hydroxynaphthalene was 6 times.

Comparative Example 1

Toluene (30 mL) and 2-hydroxynaphthalene (7.20 g) were added to a 28% aqueous sodium hydroxide solution (35.8 g), and then a 35% hydrogen peroxide solution (29.1 g) was dropwise added thereto at 45° C. over 4 hours. 2-Hydroxy-1,4-naphthoquinone was not prepared. Herein, the molar ratio of the alkali to 2-hydroxynaphthalene was 5 times; and the molar ratio of hydrogen peroxide to 2-hydroxynaphthalene was 6 times.

Comparative Example 2

Vanadium (V) oxide (273 mg), toluene (30 mL), and 2-hydroxynaphthalene (7.20 g) were added to water (35.8 g), and a 35% hydrogen peroxide solution (29.1 g) was dropwise added thereto at 45° C. over 4 hours. The mixture was subjected to the same treatment as in Example 1 to obtain a material in a tar form. NMR merely demonstrated that 2-hydroxy-1,4-naphthoquinone was generated in a yield of 5% or less. Herein, the amount of the vanadium catalyst was 3.8 mass % in relation to 2-hydroxynaphthalene; and the molar ratio of hydrogen peroxide to 2-hydroxynaphthalene was 6 times.

As described above, the production method of the present invention is a method of producing 2-hydroxy-1,4-naphthoquinone, which is an intermediate compound for producing an industrially useful compound, in a high yield and a high purity.

What is claimed is:

1. A method of producing 2-hydroxy-1,4-naphthoquinone represented by Formula [I]:

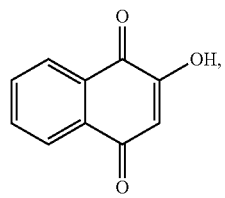

mixing 2-hydroxynaphthalene represented by Formula [II]:

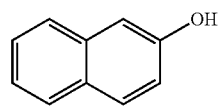

with (1) a 20% to 30% alkaline aqueous solution or (2) a mixture of a 20% to 30% alkaline aqueous solution with an inert organic solvent incompatible with water, in the presence of a vanadium catalyst so as to form an alkaline mixed aqueous solution; and adding 30% to 40% hydrogen peroxide to the alkaline mixed aqueous solution in an amount of 3 to 10 times in relation to 2- hydroxynaphthalene so as to oxidize 2-hydroxynaphthalene.

2. The method according to claim 1, wherein the alkaline aqueous solution is an aqueous solution of sodium hydroxide or potassium hydroxide.

3. The method according to claim 1, wherein the vanadium catalyst is vanadium (V) oxide.

4. The method according to claim 1, wherein the organic solvent is an aliphatic hydrocarbon, an aliphatic cyclic hydrocarbon, or an aromatic hydrocarbon.

* * * * *